United States Patent
Guntzer et al.

(10) Patent No.: US 9,895,130 B2
(45) Date of Patent: Feb. 20, 2018

(54) WATER EQUIVALENT DIAMETER DETERMINATION FROM SCOUT IMAGES

(71) Applicant: General Electric Company, Schenectady, NY (US)

(72) Inventors: Pierre Guntzer, Strasbourg (FR); Vincent Pangon, Strausbourg (FR); Benedicte Archambault, Strausbourg (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 14/946,077

(22) Filed: Nov. 19, 2015

(65) Prior Publication Data

US 2017/0143291 A1     May 25, 2017

(51) Int. Cl.
   *A61B 6/00*           (2006.01)
   *A61B 6/03*           (2006.01)
   *G06T 7/00*           (2017.01)

(52) U.S. Cl.
CPC ............ *A61B 6/5294* (2013.01); *A61B 6/032* (2013.01); *A61B 6/488* (2013.01); *A61B 6/542* (2013.01); *A61B 6/566* (2013.01); *A61B 6/465* (2013.01); *A61B 6/467* (2013.01); *G06T 7/0012* (2013.01)

(58) Field of Classification Search
CPC ....... A61B 6/032; A61B 6/5294; A61B 6/542; A61B 2576/00; A61B 6/488; A61B 6/566; A61B 6/465; A61B 6/467; G06T 7/0012
See application file for complete search history.

(56) References Cited

U.S. PATENT DOCUMENTS

| | | |
|---|---|---|
| 6,529,622 B1 | 3/2003 | Pourjavid |
| 2005/0135707 A1 | 6/2005 | Turek et al. |
| 2007/0071172 A1 | 3/2007 | Mollus et al. |
| 2011/0007980 A1 | 1/2011 | Fahimian et al. |

(Continued)

FOREIGN PATENT DOCUMENTS

WO     2008017076 A2     2/2008

OTHER PUBLICATIONS

Bibliographic information page for the AAPM Report No. 220, "Use of Water Equivalent Diameter for Calculating Patient Size and Size-Specific Dose Estimates (SSDE) in CT" by McCollough et al.*

(Continued)

*Primary Examiner* — Jon Chang

(57) ABSTRACT

Systems, methods, and computer program products that enable calculating the water equivalent diameter of an exposed subject by defining a patient object using anterior/posterior (AP) and lateral (LAT) scout images are provided. Pixels corresponding to air in the LAT and AP scout image are determined. Pixels outside the of the air area belong to either to the patient or the table. The table for both the LAT and AP scout images is identified. The remaining pixels in the LAT AP scout images are from the patient. For each segmented object (patient or table) the boundaries of the segmented object are identified and the attenuations within the segmented boundaries are computed. The final shape and attenuation values of the patient is stored and the size-specific dose estimate (SSDE) is calculated. The water equivalent diameter value is normalized by using the technical acquisition parameters provided by the acquisition device.

15 Claims, 8 Drawing Sheets

(56) References Cited

U.S. PATENT DOCUMENTS

2012/0230576 A1* 9/2012 Rohler .................. A61B 6/032
                                                       382/132
2014/0270053 A1* 9/2014 Larson .................. A61B 6/032
                                                       378/4

OTHER PUBLICATIONS

Use of Water Equivalent Diameter for Calculating Patient Size and Size-Specific Dose Estimates (SSDE) in CT AAPM Task Group Report 220 AAPM, 2014.

Estimating Patient Dose from X-ray Tube Output Metrics: Automated Measurement of Patient Size from CT Images Enables Largescale Size-specific Dose Estimates Ikuta I, Warden GI, Andriole KP, Khorasani R, Sodickson A. Radiology: vol. 270: No. 2—Feb. 2014.

Size-specific Dose Estimates for Chest, Abdominal, and Pelvic CT: Effect of Intrapatient Variability in Water-equivalent Diameter Shuai Leng, Maria Shiung, Xinhui Duan, Lifeng Yu, Yi Zhang, Cynthia H. McCollough.

International Search Report and Written Opinion for International Application No. PCT/US2016/060942 dated Feb. 15, 2017. 13 pages.

* cited by examiner

WATER EQUIVALENT DIAMETER DETERMINATION FROM SCOUT IMAGES

FIELD OF DISCLOSURE

The present disclosure relates to ionizing radiation (e.g. x-rays), and more particularly to systems, methods and computer program products to manage direction of ionizing radiation dose toward an exposed subject.

BACKGROUND

The statements in this section merely provide background information related to the disclosure and may not constitute prior art.

In non-invasive imaging systems, x-ray tubes are used in various x-ray systems and computed tomography (CT) systems as a source of ionizing (x-ray) radiation. The ionizing radiation is emitted in response to control signals during an examination or imaging sequence. An emitter within the cathode may emit a stream of electrons in response to heat resulting from an applied electrical current, and/or an electric field resulting from an applied voltage to a properly shaped metallic plate in front of the emitter. The anode may include a target that is impacted by the stream of electrons. The target may, as a result of impact by the electron beam, produce x-ray radiation to be emitted toward an imaged volume. In such imaging systems, a portion of the radiation passes through a subject of interest, such as a patient, baggage, or an article of manufacture, and impacts a digital detector or a photographic plate where the image data is collected. The signals may then be processed to generate an image that may be displayed for review. In other systems, such as systems for oncological radiation treatment, a source of x-rays may be used to direct ionizing radiation toward a target tissue. Regardless of the type of x-ray system used, it may be beneficial to know the amount (dose) of x-ray exposure during individual imaging or treatment events.

Accordingly, one concern with ionizing radiation includes an increased likelihood of harm or injury associated with radiation-induced injury to the tissue of the exposed subject. A variable that affects a likelihood of causing radiation-induced injury to tissue of an exposed subject is the dose or amount of radiation absorbed by the exposed subject. Variables that affect a dose of radiation absorbed by the exposed subject include a rate of delivery of radiation, a time of exposure of radiation, a fraction of radiation absorbed by the exposed subject, age, or other characteristics of the exposed subject, and location of radiation exposure on the exposed subject. Another concern with use of ionizing radiation includes an increased likelihood of causing effects (e.g., radiation—induced cancers) to the exposed subject.

BRIEF SUMMARY

In view of the above, there is a need for systems, methods and computer program products to improve the knowledge used to manage irradiation of the exposed subject for different applications (e.g., CT imaging of various exposed areas (e.g., chest, arms, legs, etc.) of and exposed subject). The disclosed systems, methods, and computer program products perform water equivalent diameter determination to improve the dose estimation to an exposed subject usually provided by CT dose index volume ($CTDI_{vol}$). The above-mentioned needs are addressed by the subject matter described herein and will be understood in the following specification.

According to one aspect of the present disclosure, a system that allows the determination the water equivalent diameter from anterior-posterior and lateral images is provided.

According to another aspect of the present disclosure, a method that allows the determination of the water equivalent diameter from anterior-posterior and lateral images is provided.

This summary briefly describes aspects of the subject matter described below in the Detailed Description, and is not intended to be used to limit the scope of the subject matter described in the present disclosure.

BRIEF DESCRIPTION OF THE DRAWINGS

The features and technical aspects of the system and method disclosed herein will become apparent in the following Detailed Description set forth below when taken in conjunction with the drawings in which like reference numerals indicate identical or functionally similar elements.

DETAILED DESCRIPTION

Figure 1:
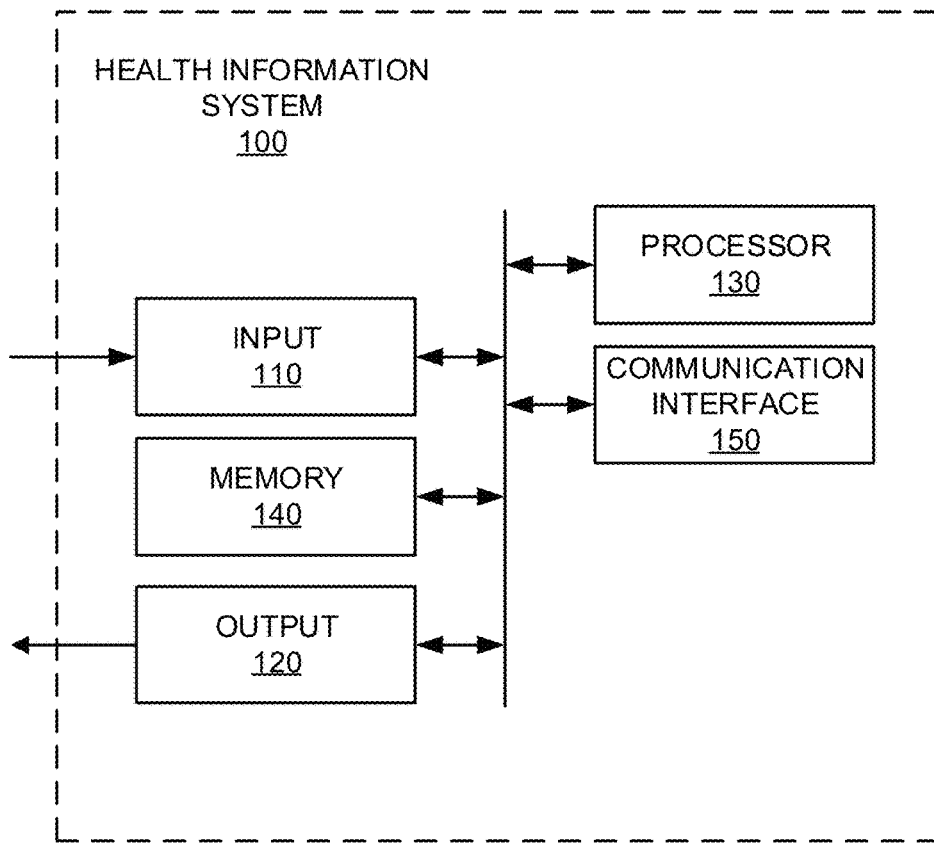
FIG. 1 shows a block diagram of an example healthcare-focused information system.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

I. Overview

For computed tomography (CT), one example metric/method to estimate irradiation dose normalized with patient anatomy is water equivalent diameter. This method consists of determining the diameter of a cylinder of water which has the same x-ray attenuation as the patient in the irradiated region. The aim is to normalize the standard CT dose index volume ($CTDI_{vol}$) dose metric according to the nature of the tissues crossed.

A DICOM image file generally includes a collection or series of tags where each tag includes a location of pixel data having a value that represents the pixel associated with the tag. The remaining tags of s DICOM image file, other than the pixel data tags, are referred to as metadata. The pixel tags of the DICOM image can represent a DICOM scout or localizer image (also referred to as a "scout image" or "localizer"). This kind of image can be sent by a device in combination with a series of image slices. In certain examples, the scout image can be a two-dimensional DICOM image of an orientation (e.g., defined by x and y axes) having been acquired along an x-axis of the CT device, which corresponds to a horizontal axis extending in a direction from a left-hand border to a right-hand border of a surface of the table, and a y-axis which corresponds to a vertical axis extending in a direction from the floor upward in direction toward a top of the table. One example, of an acquired image file includes a series of images containing the scout image as well as other images.

Water equivalent diameter can be computed from a given axial slice using the CT metadata contained in the corresponding axial slices, as these CT numbers are directly related to attenuation. However, using the axial slices has the disadvantage of requiring huge amounts of data from the hospital network and storing the data. In addition, axial slices routinely provide limited information due to the truncation of the patient on the field of view.

Scout images do not have these limitations. Each scout image corresponds to the amount of data in one single axial slice (typical cases contain hundreds of axial slices); therefore, scout images can easily be shared between systems without burdening the system in terms of both network bandwidth and data storage capacity. Also, by definition, scout images provide a complete description of the patient/target region and truncate the patient morphology by its field of view in only rare cases.

Current methods for using scout images to computer water equivalent diameter yield poor results as compared to the "Gold Standard" (e.g., water equivalent diameter computed from axial slices) due to their lesser quality attenuation information.

Aspects disclosed and described herein enable the determination of water equivalent diameter using a set of scout images. In the present application, a water equivalent diameter estimating system using scout images of an exposed subject with diagnostic image acquisition by an imaging system is considered.

Other aspects, such as those discussed in the following and others as can be appreciated by one having ordinary skill in the art upon reading the enclosed description, are also possible.

II. Example Operating Environment

Health information, also referred to as healthcare information and/or healthcare data, relates to information generated and/or used by a healthcare entity. Health information can be information associated with health of one or more patients, for example. Health information may include protected health information (PHI), as outlined in the Health Insurance Portability and Accountability Act (HIPAA), which is identifiable as associated with a particular patient and is protected from unauthorized disclosure. Health information can be organized as internal information and external information. Internal information includes patient encounter information (e.g., patient-specific data, aggregate data, comparative data, etc.) and general healthcare operations information, etc. External information includes comparative data, expert and/or knowledge-based data, etc. Information can have both a clinical (e.g., diagnosis, treatment, prevention, etc.) and administrative (e.g., scheduling, billing, management, etc.) purpose.

Institutions, such as healthcare institutions, having complex network support environments and sometimes chaotically driven process flows utilize secure handling and safeguarding of the flow of sensitive information (e.g., personal privacy). A need for secure handling and safeguarding of information increases as a demand for flexibility, volume, and speed of exchange of such information grows. For example, healthcare institutions provide enhanced control and safeguarding of the exchange and storage of sensitive patient PHI and employee information between diverse locations to improve hospital operational efficiency in an operational environment typically having a chaotic-driven demand by patients for hospital services. In certain examples, patient identifying information can be masked or even stripped from certain data depending upon where the data is stored and who has access to that data. In some examples, PHI that has been "de-identified" can be re-identified based on a key and/or other encoder/decoder.

A healthcare information technology infrastructure can be adapted to service multiple business interests while providing clinical information and services. Such an infrastructure may include a centralized capability including, for example, a data repository, reporting, discreet data exchange/connectivity, "smart" algorithms, personalization/consumer decision support, etc. This centralized capability provides information and functionality to a plurality of users including medical devices, electronic records, access portals, pay for performance (P4P), chronic disease models, and clinical health information exchange/regional health information organization (HIE/RHIO), and/or enterprise pharmaceutical studies, home health, for example.

Interconnection of multiple data sources helps enable an engagement of all relevant members of a patient's care team and helps improve an administrative and management burden on the patient for managing his or her care. Particularly, interconnecting the patient's electronic medical record and/or other medical data can help improve patient care and management of patient information. Furthermore, patient care compliance is facilitated by providing tools that automatically adapt to the specific and changing health conditions of the patient and provide comprehensive education and compliance tools to drive positive health outcomes.

In certain examples, healthcare information can be distributed among multiple applications using a variety of database and storage technologies and data formats. To provide a common interface and access to data residing across these applications, a connectivity framework (CF) can be provided which leverages common data and service models (CDM and CSM) and service oriented technologies, such as an enterprise service bus (ESB) to provide access to the data.

In certain examples, a variety of user interface frameworks and technologies can be used to build applications for health information systems including, but not limited to, MICROSOFT® ASP.NET, AJAX®, MICROSOFT® Windows Presentation Foundation, GOOGLE® Web Toolkit, MICROSOFT® Silverlight, ADOBE®, and others. Applications can be composed from libraries of information widgets to display multi-content and multi-media information, for example. In addition, the framework enables users to tailor layout of applications and interact with underlying data.

In certain examples, an advanced Service-Oriented Architecture (SOA) with a modern technology stack helps provide robust interoperability, reliability, and performance. Example SOA includes a three-fold interoperability strategy including a central repository (e.g., a central repository built from Health Level Seven (HL7) transactions), services for working in federated environments, and visual integration with third-party applications. Certain examples provide portable content enabling plug 'n play content exchange among healthcare organizations. A standardized vocabulary using common standards (e.g., LOINC, SNOMED CT, RxNorm, FDB, ICD-9, ICD-10, etc.) is used for interoperability, for example. Certain examples provide an intuitive user interface to help minimize end-user training. Certain examples facilitate user-initiated launching of third-party applications directly from a desktop interface to help provide a seamless workflow by sharing user, patient, and/or other contexts. Certain examples provide real-time (or at least substantially real time assuming some system delay) patient data from one or more information technology (IT) systems and facilitate comparison(s) against evidence-based best practices. Certain examples provide one or more dashboards for specific sets of patients. Dashboard(s) can be based on condition, role, and/or other criteria to indicate variation(s) from a desired practice, for example.

A. Example Healthcare Information System

An information system can be defined as an arrangement of information/data, processes, and information technology that interact to collect, process, store, and provide informational output to support delivery of healthcare to one or more patients. Information technology includes computer technology (e.g., hardware and software) along with data and telecommunications technology (e.g., data, image, and/or voice network, etc.).

Turning now to the figures, FIG. 1 shows a block diagram of an example healthcare-focused information system 100. Example system 100 can be configured to implement a variety of systems and processes including image storage (e.g., picture archiving and communication system (PACS), etc.), image processing and/or analysis, radiology reporting and/or review (e.g., radiology information system (RIS), etc.), computerized provider order entry (CPOE) system, clinical decision support, patient monitoring, population health management (e.g., population health management system (PHMS), health information exchange (HIE), etc.), healthcare data analytics, cloud-based image sharing, electronic medical record (e.g., electronic medical record system (EMR), electronic health record system (EHR), electronic patient record (EPR), personal health record system (PHR), etc.), and/or other health information system (e.g., clinical information system (CIS), hospital information system (HIS), patient data management system (PDMS), laboratory information system (LIS), cardiovascular information system (CVIS), etc.

As illustrated in FIG. 1, the example information system 100 includes an input 110, an output 120, a processor 130, a memory 140, and a communication interface 150. The components of example system 100 can be integrated in one device or distributed over two or more devices.

Example input 110 may include a keyboard, a touch-screen, a mouse, a trackball, a track pad, optical barcode recognition, voice command, etc. or combination thereof used to communicate an instruction or data to system 100. Example input 110 may include an interface between systems, between user(s) and system 100, etc.

Example output 120 can provide a display generated by processor 130 for visual illustration on a monitor or the like. The display can be in the form of a network interface or graphic user interface (GUI) to exchange data, instructions, or illustrations on a computing device via communication interface 150, for example. Example output 120 may include a monitor (e.g., liquid crystal display (LCD), plasma display, cathode ray tube (CRT), etc.), light emitting diodes (LEDs), a touch-screen, a printer, a speaker, or other conventional display device or combination thereof.

Example processor 130 includes hardware and/or software configuring the hardware to execute one or more tasks and/or implement a particular system configuration. Example processor 130 processes data received at input 110 and generates a result that can be provided to one or more of output 120, memory 140, and communication interface 150. For example, example processor 130 can take user annotation provided via input 110 with respect to an image displayed via output 120 and can generate a report associated with the image based on the annotation. As another example, processor 130 can process updated patient information obtained via input 110 to provide an updated patient record to an EMR via communication interface 150.

Example memory 140 may include a relational database, an object-oriented database, a data dictionary, a clinical data repository, a data warehouse, a data mart, a vendor neutral archive, an enterprise archive, etc. Example memory 140 stores images, patient data, best practices, clinical knowledge, analytics, reports, etc. Example memory 140 can store data and/or instructions for access by the processor 130. In certain examples, memory 140 can be accessible by an external system via the communication interface 150.

In certain examples, memory 140 stores and controls access to encrypted information, such as patient records, encrypted update-transactions for patient medical records, including usage history, etc. In an example, medical records can be stored without using logic structures specific to medical records. In such a manner, memory 140 is not searchable. For example, a patient's data can be encrypted with a unique patient-owned key at the source of the data. The data is then uploaded to memory 140. Memory 140 does not process or store unencrypted data thus minimizing privacy concerns. The patient's data can be downloaded and decrypted locally with the encryption key.

For example, memory 140 can be structured according to provider, patient, patient/provider association, and document. Provider information may include, for example, an identifier, a name, and address, a public key, and one or more security categories. Patient information may include, for example, an identifier, a password hash, and an encrypted email address. Patient/provider association information may include a provider identifier, a patient identifier, an encrypted key, and one or more override security categories. Document information may include an identifier, a patient identifier, a clinic identifier, a security category, and encrypted data, for example.

Example communication interface 150 facilitates transmission of electronic data within and/or among one or more systems. Communication via communication interface 150 can be implemented using one or more protocols. In some examples, communication via communication interface 150 occurs according to one or more standards (e.g., Digital Imaging and Communications in Medicine (DICOM), Health Level Seven (HL7), ANSI X12N, etc.). Example communication interface 150 can be a wired interface (e.g., a data bus, a Universal Serial Bus (USB) connection, etc.) and/or a wireless interface (e.g., radio frequency, infrared, near field communication (NFC), etc.). For example, communication interface 150 may communicate via wired local area network (LAN), wireless LAN, wide area network (WAN), etc. using any past, present, or future communication protocol (e.g., BLUETOOTH™, USB 2.0, USB 3.0, etc.).

In certain examples, a Web-based portal may be used to facilitate access to information, patient care and/or practice management, etc. Information and/or functionality available via the Web-based portal may include one or more of order entry, laboratory test results review system, patient information, clinical decision support, medication management, scheduling, electronic mail and/or messaging, medical resources, etc. In certain examples, a browser-based interface can serve as a zero footprint, zero download, and/or other universal viewer for a client device.

In certain examples, the Web-based portal serves as a central interface to access information and applications, for example. Data may be viewed through the Web-based portal or viewer, for example. Additionally, data may be manipulated and propagated using the Web-based portal, for example. Data may be generated, modified, stored and/or used and then communicated to another application or system to be modified, stored and/or used, for example, via the Web-based portal, for example.

The Web-based portal may be accessible locally (e.g., in an office) and/or remotely (e.g., via the Internet and/or other private network or connection), for example. The Web-based portal may be configured to help or guide a user in accessing data and/or functions to facilitate patient care and practice management, for example. In certain examples, the Web-based portal may be configured according to certain rules, preferences and/or functions, for example. For example, a user may customize the Web portal according to particular desires, preferences and/or requirements.

B. Example Healthcare Infrastructure

Figure 2:
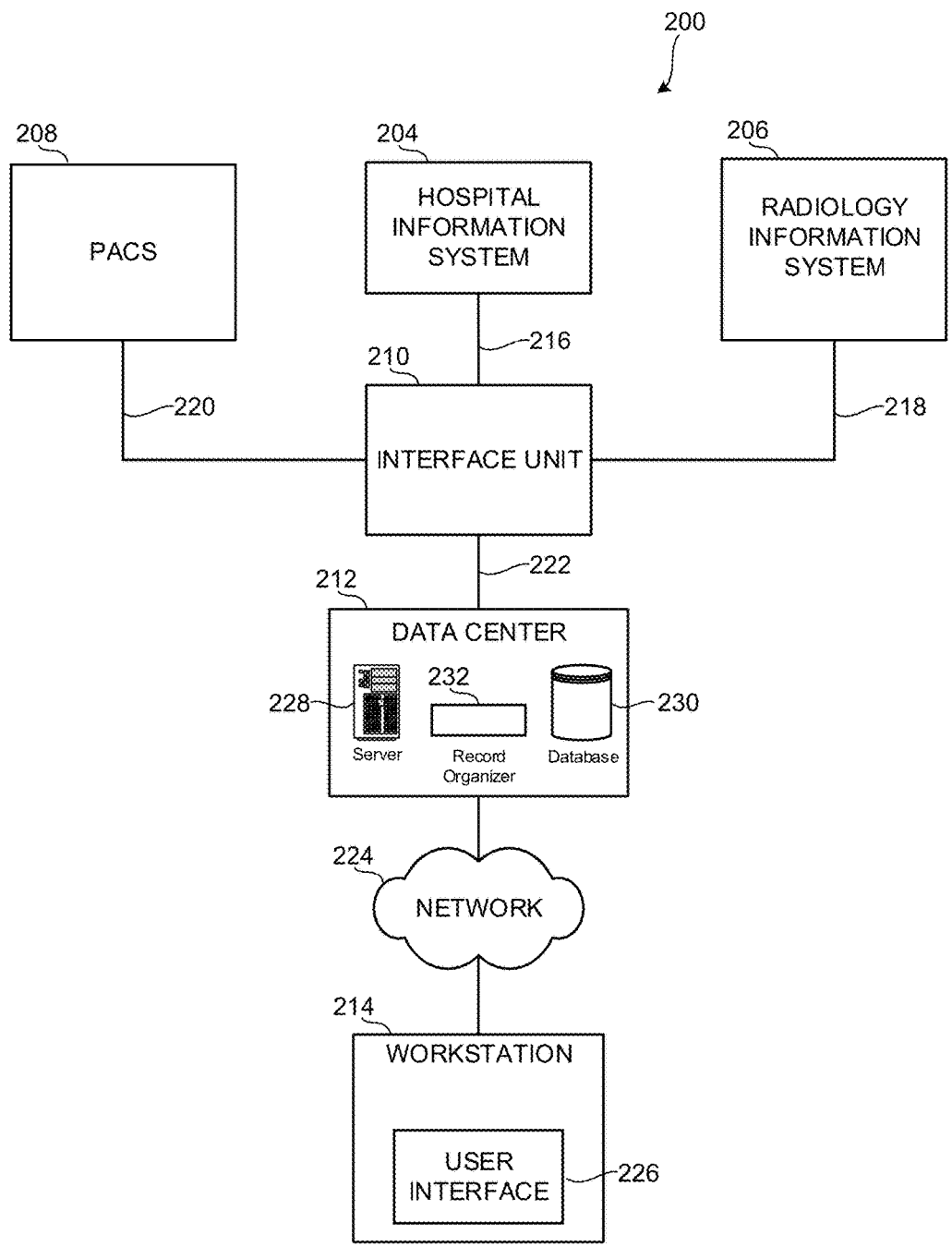
FIG. 2 shows a block diagram of an example healthcare information infrastructure including one or more systems.

FIG. 2 shows a block diagram of an example healthcare information infrastructure 200 including one or more subsystems such as the example healthcare-related information system 100 illustrated in FIG. 1. Example healthcare system 200 includes a HIS 204, a RIS 206, a PACS 208, an interface unit 210, a data center 212, and a workstation 214. In the illustrated example, HIS 204, RIS 206, and PACS 208 are housed in a healthcare facility and locally archived. However, in other implementations, HIS 204, RIS 206, and/or PACS 208 may be housed within one or more other suitable locations. In certain implementations, one or more of PACS 208, RIS 206, HIS 204, etc., may be implemented remotely via a thin client and/or downloadable software solution. Furthermore, one or more components of the healthcare system 200 can be combined and/or implemented together. For example, RIS 206 and/or PACS 208 can be integrated with HIS 204; PACS 208 can be integrated with RIS 206; and/or the three example information systems 204, 206, and/or 208 can be integrated together. In other example implementations, healthcare system 200 includes a subset of the illustrated information systems 204, 206, and/or 208. For example, healthcare system 200 may include only one or two of HIS 204, RIS 206, and/or PACS 208. Information (e.g., scheduling, test results, exam image data, observations, diagnosis, etc.) can be entered into HIS 204, RIS 206, and/or PACS 208 by healthcare practitioners (e.g., radiologists, physicians, and/or technicians) and/or administrators before and/or after patient examination.

The HIS 204 stores medical information such as clinical reports, patient information, and/or administrative information received from, for example, personnel at a hospital, clinic, and/or a physician's office (e.g., an EMR, EHR, PHR, etc.). RIS 206 stores information such as, for example, radiology reports, radiology exam image data, messages, warnings, alerts, patient scheduling information, patient demographic data, patient tracking information, and/or physician and patient status monitors. Additionally, RIS 206 enables exam order entry (e.g., ordering an x-ray of a patient) and image and film tracking (e.g., tracking identities of one or more people that have checked out a film). In some examples, information in RIS 206 is formatted according to the HL-7 (Health Level Seven) clinical communication protocol. In certain examples, a medical exam distributor is located in RIS 206 to facilitate distribution of radiology exams to a radiologist workload for review and management of the exam distribution by, for example, an administrator.

PACS 208 stores medical images (e.g., x-rays, scans, three-dimensional renderings, etc.) as, for example, digital images in a database or registry. In some examples, the medical images are stored in PACS 208 using the Digital Imaging and Communications in Medicine (DICOM) format. Images are stored in PACS 208 by healthcare practitioners (e.g., imaging technicians, physicians, radiologists) after a medical imaging of a patient and/or are automatically transmitted from medical imaging devices to PACS 208 for storage. In some examples, PACS 208 can also include a display device and/or viewing workstation to enable a healthcare practitioner or provider to communicate with PACS 208.

The interface unit 210 includes a hospital information system interface connection 216, a radiology information system interface connection 218, a PACS interface connection 220, and a data center interface connection 222. Interface unit 210 facilities communication among HIS 204, RIS 206, PACS 208, and/or data center 212. Interface connections 216, 218, 220, and 222 can be implemented by, for example, a Wide Area Network (WAN) such as a private network or the Internet. Accordingly, interface unit 210 includes one or more communication components such as, for example, an Ethernet device, an asynchronous transfer mode (ATM) device, an 802.11 device, a DSL modem, a cable modem, a cellular modem, etc. In turn, the data center 212 communicates with workstation 214, via a network 224, implemented at a plurality of locations (e.g., a hospital, clinic, doctor's office, other medical office, or terminal, etc.). Network 224 is implemented by, for example, the Internet, an intranet, a private network, a wired or wireless Local Area Network, and/or a wired or wireless Wide Area Network. In some examples, interface unit 210 also includes a broker (e.g., a Mitra Imaging's PACS Broker) to allow medical information and medical images to be transmitted together and stored together.

Interface unit 210 receives images, medical reports, administrative information, exam workload distribution information, and/or other clinical information from the information systems 204, 206, 208 via the interface connections 216, 218, 220. If necessary (e.g., when different formats of the received information are incompatible), interface unit 210 translates or reformats (e.g., into Structured Query Language ("SQL") or standard text) the medical information, such as medical reports, to be properly stored at data center 212. The reformatted medical information can be transmitted using a transmission protocol to enable different medical information to share common identification elements, such as a patient name or social security number. Next, interface unit 210 transmits the medical information to data center 212 via data center interface connection 222. Finally, medical information is stored in data center 212 in, for example, the DICOM format, which enables medical images and corresponding medical information to be transmitted and stored together.

The medical information is later viewable and easily retrievable at workstation 214 (e.g., by their common identification element, such as a patient name or record number). Workstation 214 can be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. Workstation 214 receives commands and/or other input from a user via, for example, a keyboard, mouse, track ball, microphone, etc. Workstation 214 is capable of implementing a user interface 226 to enable a healthcare practitioner and/or administrator to interact with healthcare system 200. For example, in response to a request from a physician, user interface 226 presents a patient medical history. In other examples, a radiologist is able to retrieve and manage a workload of exams distributed for review to the radiologist via user interface 226. In further examples, an administrator reviews radiologist workloads, exam allocation, and/or operational statistics associated with the distribution of exams via user interface 226. In some examples, the administrator adjusts one or more settings or outcomes via user interface 226.

Example data center 212 of FIG. 2 is an archive to store information such as images, data, medical reports, and/or, more generally, patient medical records. In addition, data center 212 can also serve as a central conduit to information located at other sources such as, for example, local archives, hospital information systems/radiology information systems (e.g., HIS 204 and/or RIS 206), or medical imaging/storage systems (e.g., PACS 208 and/or connected imaging modalities). That is, the data center 212 can store links or indicators (e.g., identification numbers, patient names, or record numbers) to information. In the illustrated example, data center 212 is managed by an application server provider (ASP) and is located in a centralized location that can be accessed by a plurality of systems and facilities (e.g., hospitals, clinics, doctor's offices, other medical offices, and/or terminals). In some examples, data center 212 can be spatially distant from HIS 204, RIS 206, and/or PACS 208.

Example data center 212 of FIG. 2 includes a server 228, a database 230, and a record organizer 232. Server 228 receives, processes, and conveys information to and from the components of healthcare system 200. Database 230 stores the medical information described herein and provides access thereto. Example record organizer 232 of FIG. 2 manages patient medical histories, for example. Record organizer 232 can also assist in procedure scheduling, for example.

Certain examples can be implemented as cloud-based clinical information systems and associated methods of use. An example cloud-based clinical information system enables healthcare entities (e.g., patients, clinicians, sites, groups, communities, and/or other entities) to share information via web-based applications, cloud storage and cloud services. For example, the cloud-based clinical information system may enable a first clinician to securely upload information into the cloud-based clinical information system to allow a second clinician to view and/or download the information via a web application. Thus, for example, the first clinician may upload an x-ray image into the cloud-based clinical information system, and the second clinician may view the x-ray image via a web browser and/or download the x-ray image onto a local information system employed by the second clinician.

In certain examples, users (e.g., a patient and/or care provider) can access functionality provided by system 200 via a software-as-a-service (SaaS) implementation over a cloud or other computer network, for example. In certain examples, all or part of system 200 can also be provided via platform as a service (PaaS), infrastructure as a service (IaaS), etc. For example, system 200 can be implemented as a cloud-delivered Mobile Computing Integration Platform as a Service. A set of consumer-facing Web-based, mobile, and/or other applications enable users to interact with the PaaS, for example.

C. Example Methods of Use

Clinical workflows are typically defined to include one or more steps or actions to be taken in response to one or more events and/or according to a schedule. Events may include receiving a healthcare message associated with one or more aspects of a clinical record, opening a record(s) for new patient(s), receiving a transferred patient, reviewing and reporting on an image, and/or any other instance and/or situation that requires or dictates responsive action or processing. The actions or steps of a clinical workflow may include placing an order for one or more clinical tests, scheduling a procedure, requesting certain information to supplement a received healthcare record, retrieving additional information associated with a patient, providing instructions to a patient and/or a healthcare practitioner associated with the treatment of the patient, radiology image reading, and/or any other action useful in processing healthcare information. The defined clinical workflows may include manual actions or steps to be taken by, for example, an administrator or practitioner, electronic actions or steps to be taken by a system or device, and/or a combination of manual and electronic action(s) or step(s). While one entity of a healthcare enterprise may define a clinical workflow for a certain event in a first manner, a second entity of the healthcare enterprise may define a clinical workflow of that event in a second, different manner. In other words, different healthcare entities may treat or respond to the same event or circumstance in different fashions. Differences in workflow approaches may arise from varying preferences, capabilities, requirements or obligations, standards, protocols, etc. among the different healthcare entities.

In certain examples, a medical exam conducted on a patient can involve review by a healthcare practitioner, such as a radiologist, to obtain, for example, diagnostic information from the exam. In a hospital setting, medical exams can be ordered for a plurality of patients, all of which require review by an examining practitioner. Each exam has associated attributes, such as a modality, a part of the human body under exam, and/or an exam priority level related to a patient criticality level. Hospital administrators, in managing distribution of exams for review by practitioners, can consider the exam attributes as well as staff availability, staff credentials, and/or institutional factors such as service level agreements and/or overhead costs.

Additional workflows can be facilitated such as bill processing, revenue cycle mgmt., population health management, patient identity, consent management, etc.

III. Example System

Figure 3:
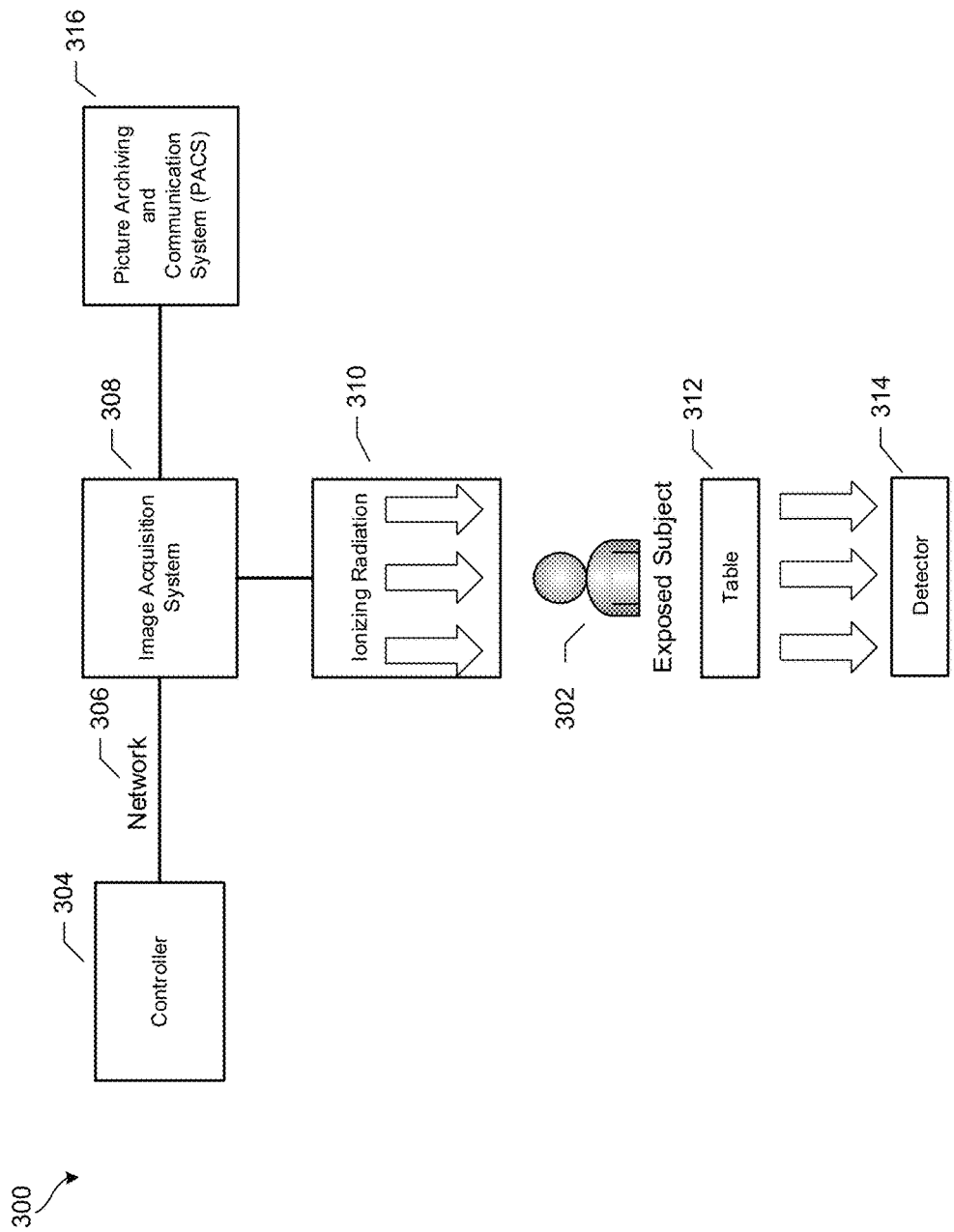
FIG. 3 is a block diagram illustrating an example system to track and report delivery of a radiation dose during or in an image acquisition procedure or other protocol involving direction of ionizing radiation toward an exposed subject.

FIG. 3 depicts an example system 300 to track and report delivery of a radiation dose during or in an image acquisition procedure or other protocol involving direction of ionizing radiation toward an exposed subject 302, according to one aspect of the present disclosure. In certain aspects, system 300 includes a controller 304 in communication via a network 306 with an image acquisition system 308 that employs ionizing radiation 310 in the generation of diagnostic images of exposed subject 302. Ionizing radiation 310 may pass through exposed subject 302 and/or table 312 before reaching detector 314.

In certain aspects, the type of image acquisition system 308 can be an angiographic imaging system, computed tomography (CT), a fluoroscopic imaging system or any other system having a radiation source projecting a beam of ionizing radiation (e.g., x-rays) toward exposed subject 302 to be received at a detector 314 in a conventional manner. The ionizing radiation can be attenuated with the passing through exposed subject 302 which the detector can translate the attenuation of ionizing radiation to generate the image data files that can conventionally display or illustrate a region of interest of the exposed subject 302 in a known manner.

Figure 4:
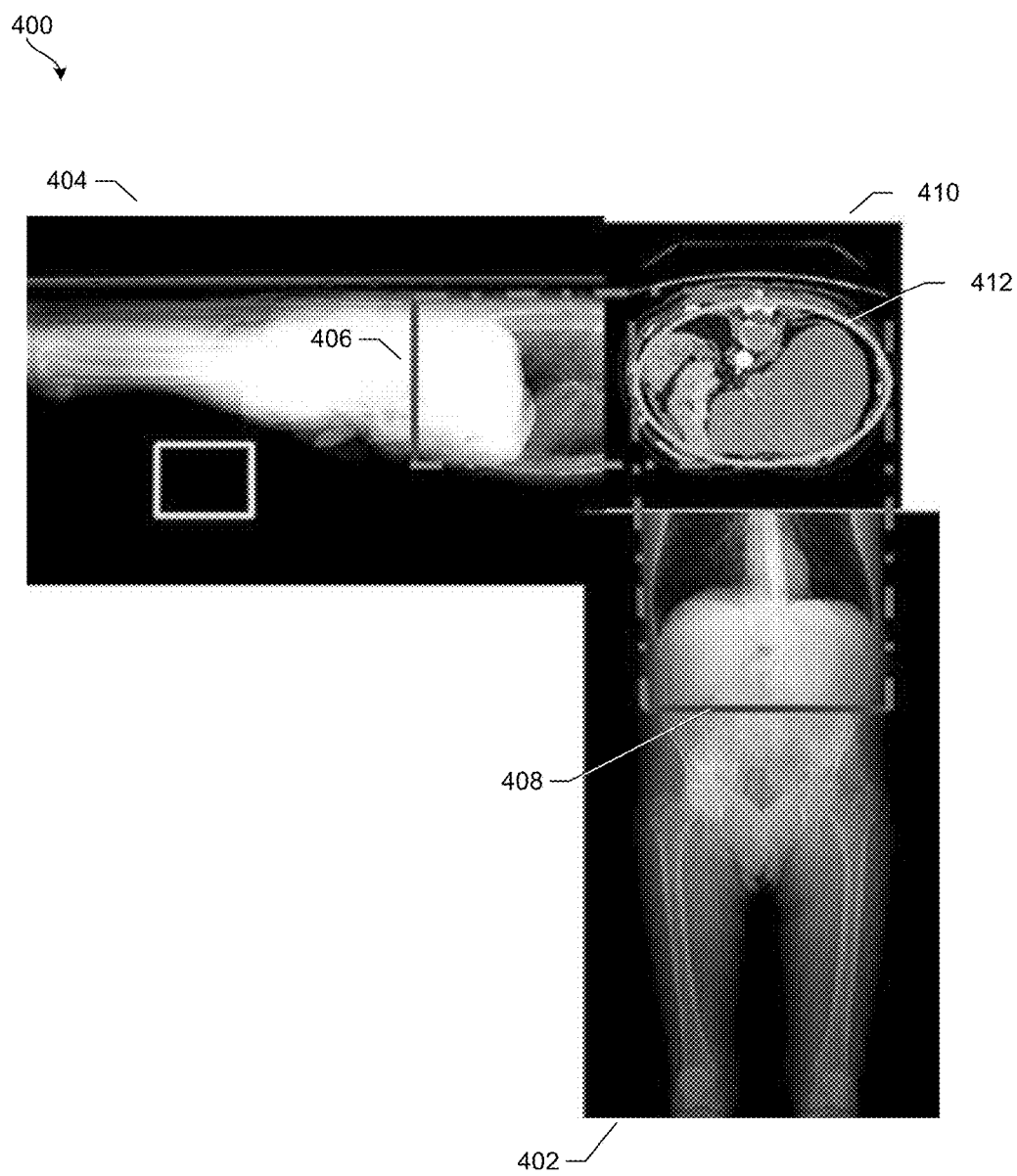
FIG. 4 shows a sample patient contour that can be used in an example method of operating the system of FIG. 3, according to the present disclosure.

Referring to FIG. 4, in certain aspects, system 300 determines the water equivalent diameter of the exposed subject 302 during an imaging procedure by using image acquisition system 308 to generate at least two scout images. In certain aspects, at least one of the scout images is a DICOM Anterior/Posterior (AP) 402 scout image and at least one of the scout images is a DICOM Lateral (LAT) 404 scout image. In certain aspects, system 300 also reports the scanning range associated with the DICOM scout images for communication to controller 304.

For example, one of the scout images can be a frontal planar view 402 (e.g., a projection image of exposed subject 302 resting on table 312) of the relevant portion of interest of exposed subject 302, while the slice images may be cross-sectional diagnostic images of exposed subject 302. In certain aspects, the scout image can be a general illustration of the projected view of exposed subject 302 that is different with respect to the slice images, the scout image generated to show a location of each of the acquired slice images relative to other acquired slices and their location with respect to exposed subject 302. The illustration of the location of each of the slice images with respect to the scout image can be indicated by, for example, a graphic line 406 or 408 created for display in the scout image. From the graphic illustration of the scout image, in certain aspects, a user can select with a pointer, mouse, or similar input device a region of interest associated with one of the series of slice images for detailed viewing. In certain aspects, the illustration of the graphic line or area in the scout image can change positions to reflect a position of the slice of current interest for detailed viewing. As well understood to one skilled in the art, each of the slices are generally similar in diagnostic image data content to other slice images associated with exposed subject 302, while the scout image is generally a very different viewpoint of exposed subject 302 and lower image resolution relative to the series of slices.

Figure 5:
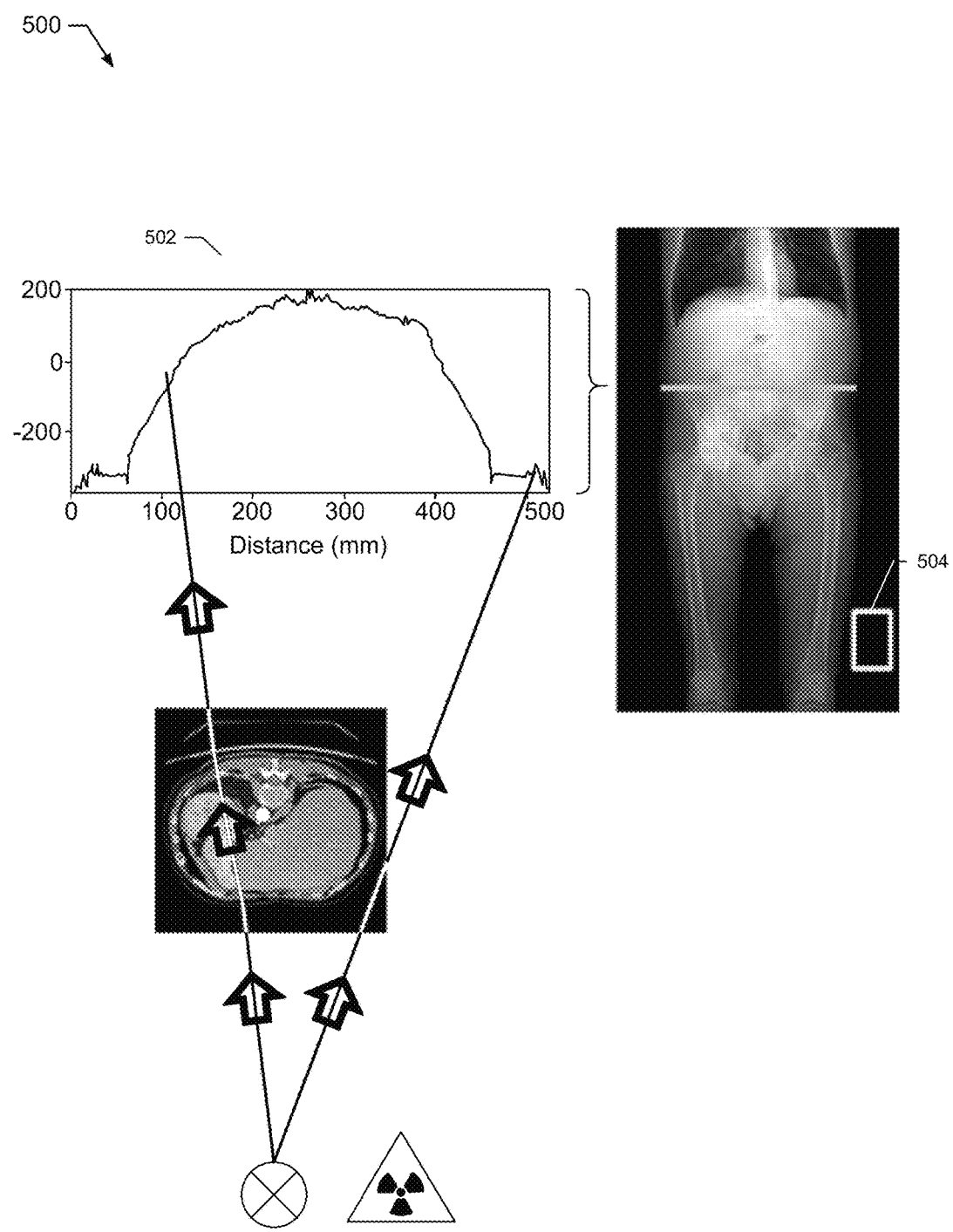
FIG. 5 shows an imaginary x-ray starting from the source and ending in the detector's plane, according to the present disclosure.

Having two scout images of the same scene under different points of view (LAT view 404 and AP view 402) allows reconstructing a reasonable 3D outer shape of patient 302 (shown in an axial slice 410, corresponding to lines 406 in LAT view 404 and 408 in AP view 402), in this example, an elliptical representation 412 of exposed subject 302. A scout image provides the sum of the voxels attenuation along a line that starts at the x-ray source and ends at the detector plane. FIG. 5 illustrates that the attenuations 502 seen on the localizer for a given z-location (402,404) are the sum of the attenuation of the voxels of both the surrounding media 504 and exposed subject 302. In certain aspects, the surrounding media is assumed to be homogeneous (air). In certain aspects, system 300 determines the attenuation contribution of the surrounding media which helps to track and report delivery of a radiation dose during or in an image acquisition procedure.

Figure 6:
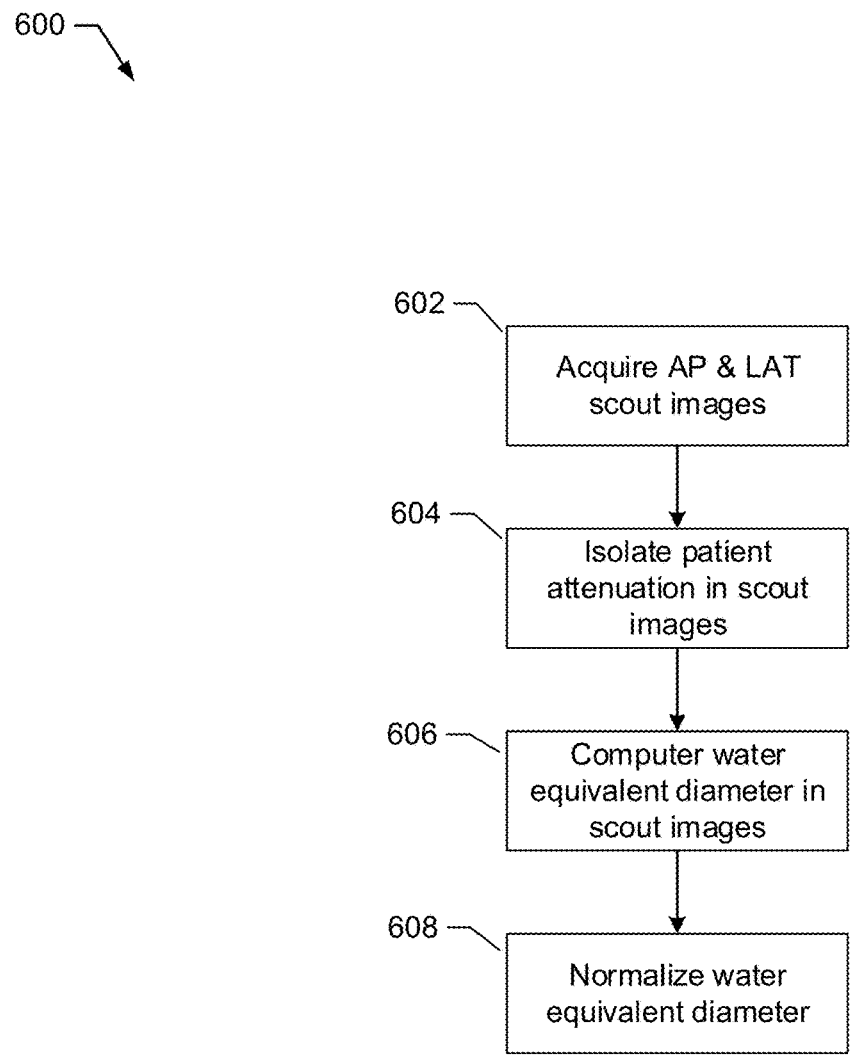
FIG. 6 shows a high-level flow chart of a method to calculate the water equivalent diameter, according to the present disclosure.

An overview of system 300 to track and report delivery of a radiation dose during or in an image acquisition procedure is illustrated in FIG. 6, the example system details the method of the water equivalent diameter of the exposed subject 302. In block 602, AP and LAT scout images are acquired from Image Acquisition System 308 or PACS 316. In block 604, image processing methods (for example, segmentation, etc.) are used to isolate the patient from the other objects present in the scout image (such as, but not limited to: table, surrounding homogeneous media like air, tubes, clothes, headrest, mattress, etc.). In block 606, water equivalent diameter Dw(loc) in the area of interest is computed from one or both of the scout images.

One example method that could be used to compute Dw(loc) consists in computing the patient attenuation µp with the mean of the Hounsfield units found in the patient Mean(Hu) and water attenuation µw:

$$\mu p = \mu w [(\text{Mean}(Hu)/1000)+1] \qquad \text{Equation 1:}$$

Water equivalent area could then be calculated from observed patient are Ap (illustrated in 412 in FIG. 4):

$$Aw = (\mu p \cdot Ap)/\mu w \qquad \text{Equation 2:}$$

Finally, water equivalent diameter in the scout image can be estimated using:

$$D_w = 2 \cdot \sqrt{\frac{A_w}{\Pi}} \qquad \text{Equation 3}$$

The method described in the instant application is not limited to this particular method for determining Dw(loc) from actual patient attenuation found in block 606; any other algorithm could be used to compute water equivalent diameter from patient attenuation.

Area of interest for water equivalent diameter could be, but is not limited to: a region at the center of a particular area of an irradiation event, the totality of the area of an irradiation event, like: tension, current, etc.

Finally, in block 608, the water equivalent diameter value is normalized by using the technical acquisition parameters provided by the acquisition device. Due to the fact that localizers and slices images are not acquired and reconstructed the same manner, we can improve the result obtained by the method by applying some additional correction factors based on empiric experimentations. Such factors are stored in look up tables and could be based on technical acquisition parameters of the acquisition. These parameters could be, but are not limited to: voltage, intensity of the current, modulation of the current, collimation width . . . .

IV. Example Method

In certain aspects, isolating patient attenuation in block 604 may include: 1) given the LAT scout image, its field of view area may have areas corresponding to x-rays that have emitted by the source and only passed through air before being collected onto the detector plane (free trajectories). As the attenuation captured by the scout image for each pixel of such area is the sum of the attenuation of the voxels along each free trajectory. Using the well-known homogeneity hypothesis, the attenuation of air voxels is known. 2) The attenuation estimate of a voxel can be averaged over all free trajectories. 3) Contour of the patient and its attenuation for each line of a given z-location is found. 4) Contour of the table and its attenuation is found.

From the AP scout image, using the contour of the patient of LAT scout image, the thickness of air crossed by x-rays before hitting the patient is known. The corresponding contribution of the air to the attenuation seen in the AP scout image can be removed (air attenuation for a voxel is known with LAT) inside the patient contour detected in the AP scout image. If a table was detected in the LAT scout image, the edges of the table are determined in the AP scout image. If not found, in certain aspects, the table is assumed to be larger than the field of view and the estimate of the table attenuation can be calculated as above and thus the table attenuation can be removed. If table edges are found in the AP scout image, the table attenuation contribution can be removed directly. Contribution of air to attenuation starting from area between exposed patient and table and stopping at the detector plane seen in the AP scout image is removed in a similar manner as described above. Using patient contour detection on the resulting AP subtracted scout image results in the determining the patient width and thus the attenuation found within the contour can be attributed to the patient itself. The patient attenuation can then be estimated from the area of the schematic shape chosen (in the example, the ellipse 412 in FIG. 4) and the water equivalent diameter for each z-location is computed.

Figure 7:
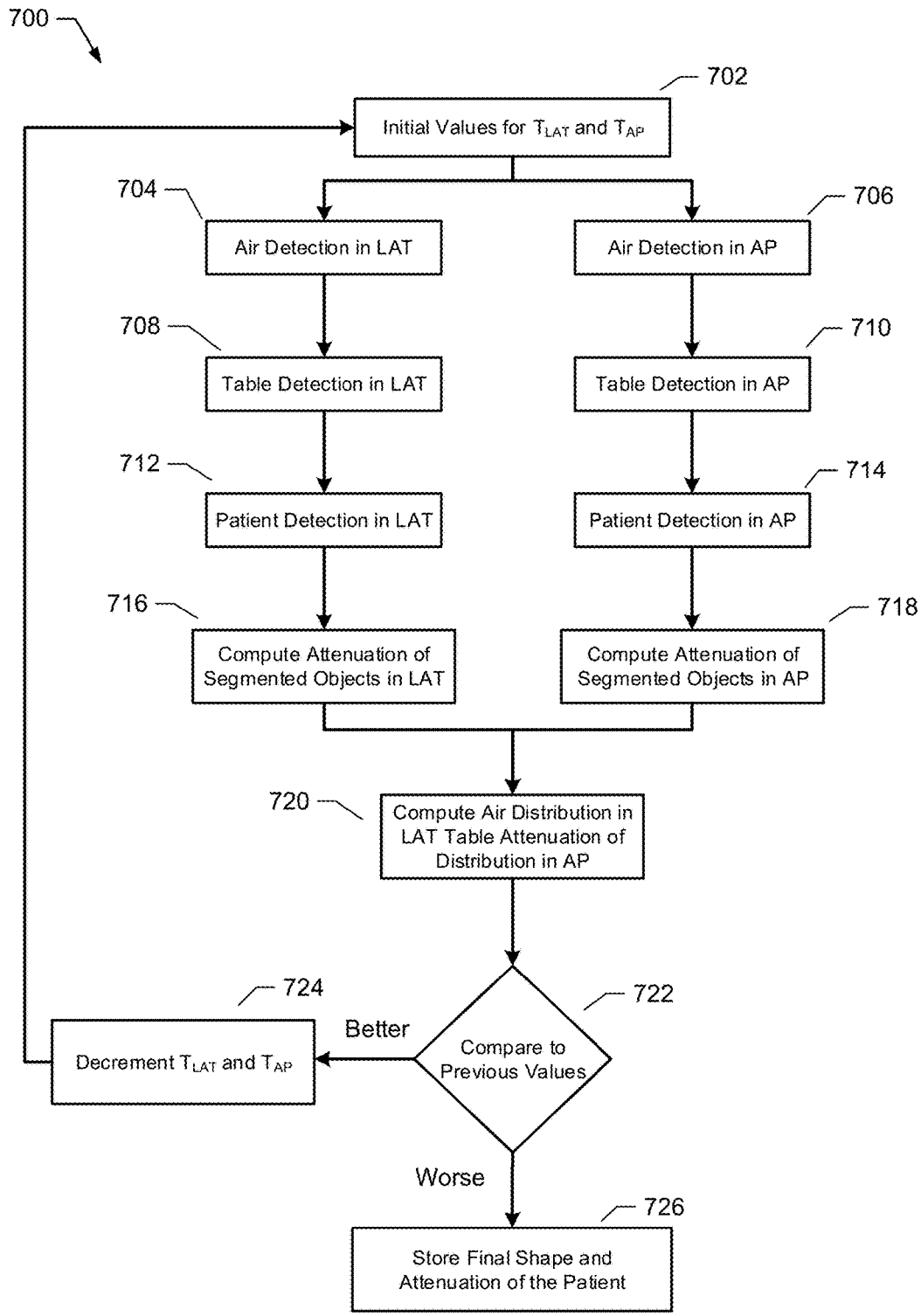
FIG. 7 shows a detailed flow chart of a method to calculate the water equivalent diameter, according to the present disclosure.

FIG. 7 illustrates a flow diagram for method 700 which calculates the water equivalent diameter of an exposed subject by defining a patient object using AP and LAT scout images in system 300 according to one aspect of the present disclosure. In block 702, high values of air thresholds are defined in Hu (Hounsfield unit) for the lateral scout image $T_{LAT}$ and the anterior/posterior scout image $T_{AP}$. In blocks 704 and 706, pixels corresponding to air in the LAT scout image are determined using $T_{LAT}$ and pixels corresponding to air in the AP scout image are determined using $T_{AP}$. Pixels outside the of the air area belong to either to the patient or the table. In blocks 708 and 710, a Hough transform is used to identify the table for both the LAT and AP scout images. The remaining pixels in the LAT scout image 712 and AP scout image 714 are from the patient. In blocks 716 and 718, for each segmented object (patient or table): for each z value of the vertical axis of the LAT and AP scout images, the boundaries of the segmented object are identified and the attenuations within the segmented boundaries are computed. In block 720, the air attenuation values in the LAT scout image are computed. Next, the table attenuation values in the LAT scout image are computed. Then, the table attenuation in the AP scout image is computed by first determining the air attenuation in the AP scout image. If there is no air detected use the air attenuation value from the LAT scout image. In the area where there is a table with no patient, the air attenuation is subtracted in the AP scout image leaving only the attenuation due to the table. In block 722, previous air attenuation distribution and previous table attenuation distribution in the LAT image, along with the previous table attenuation in the AP scout image is compared to the values computed in block 720. If previous values do not show a more centered distribution (less and higher peaks after a Gaussian transform, for example) the $T_{LAT}$ and $T_{AP}$ values are decremented 724 and the process begins again using these values in block 702. If the previous values do show a more centered distribution, the final shape and attenuation values of the patient is stored and the size-specific dose estimate (SSDE) is calculated. The water equivalent diameter value is normalized by using the technical acquisition parameters provided by the acquisition device. Due to the fact that localizers and slices images are not acquired and reconstructed the same manner, we can improve the result obtained by the method by applying some additional correction factors based on empiric experimentations. Such factors are stored in look up tables and could be based on technical acquisition parameters of the acquisition. These parameters could be, but are not limited to: voltage, intensity of the current, modulation of the current, and collimation width.

In these examples, the machine readable instructions comprise a program for execution by a processor such as processor 812 shown in the example processor platform 800 discussed below in connection with FIG. 8. The program can be embodied in software stored on a tangible computer readable storage medium such as a CD-ROM, a floppy disk, a hard drive, a digital versatile disk (DVD), a BLU-RAY™ disk, or a memory associated with processor 812, but the entire program and/or parts thereof could alternatively be executed by a device other than processor 812 and/or embodied in firmware or dedicated hardware. Further, although the example program is described with reference to the flowchart illustrated in FIG. 7, many other methods of implementing the example system-wide probabilistic alerting and activation can alternatively be used. For example, the order of execution of the blocks can be changed, and/or some of the blocks described can be changed, eliminated, or combined.

As mentioned above, the example processes of FIG. 8 can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIG. 7 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

V. Computing Device

The subject matter of this description may be implemented as stand-alone system or for execution as an application capable of execution by one or more computing devices. The application (e.g., webpage, downloadable applet or other mobile executable) can generate the various displays or graphic/visual representations described herein as graphic user interfaces (GUIs) or other visual illustrations, which may be generated as webpages or the like, in a manner to facilitate interfacing (receiving input/instructions, generating graphic illustrations) with users via the computing device(s).

Memory and processor as referred to herein can be stand-alone or integrally constructed as part of various programmable devices, including for example a desktop computer or laptop computer hard-drive, field-programmable gate arrays (FPGAs), application-specific integrated circuits (ASICs), application-specific standard products (ASSPs), system-on-a-chip systems (SOCs), programmable logic devices (PLDs), etc. or the like or as part of a Computing Device, and any combination thereof operable to execute the instructions associated with implementing the method of the subject matter described herein.

Computing device as referenced herein may include: a mobile telephone; a computer such as a desktop or laptop type; a Personal Digital Assistant (PDA) or mobile phone; a notebook, tablet or other mobile computing device; or the like and any combination thereof.

Computer readable storage medium or computer program product as referenced herein is tangible (and alternatively as non-transitory, defined above) and may include volatile and non-volatile, removable and non-removable media for storage of electronic-formatted information such as computer readable program instructions or modules of instructions, data, etc. that may be stand-alone or as part of a computing device. Examples of computer readable storage medium or computer program products may include, but are not limited to, RAM, ROM, EEPROM, Flash memory, CD-ROM, DVD-ROM or other optical storage, magnetic cassettes, magnetic tape, magnetic disk storage or other magnetic storage devices, or any other medium which can be used to store the desired electronic format of information and which can be accessed by the processor or at least a portion of the computing device.

The terms module and component as referenced herein generally represent program code or instructions that causes specified tasks when executed on a processor. The program code can be stored in one or more computer readable mediums.

Network as referenced herein may include, but is not limited to, a wide area network (WAN); a local area network (LAN); the Internet; wired or wireless (e.g., optical, Bluetooth, radio frequency (RF)) network; a cloud-based computing infrastructure of computers, routers, servers, gateways, etc.; or any combination thereof associated therewith that allows the system or portion thereof to communicate with one or more computing devices.

The term user and/or the plural form of this term is used to generally refer to those persons capable of accessing, using, or benefiting from the present disclosure.

Figure 8:
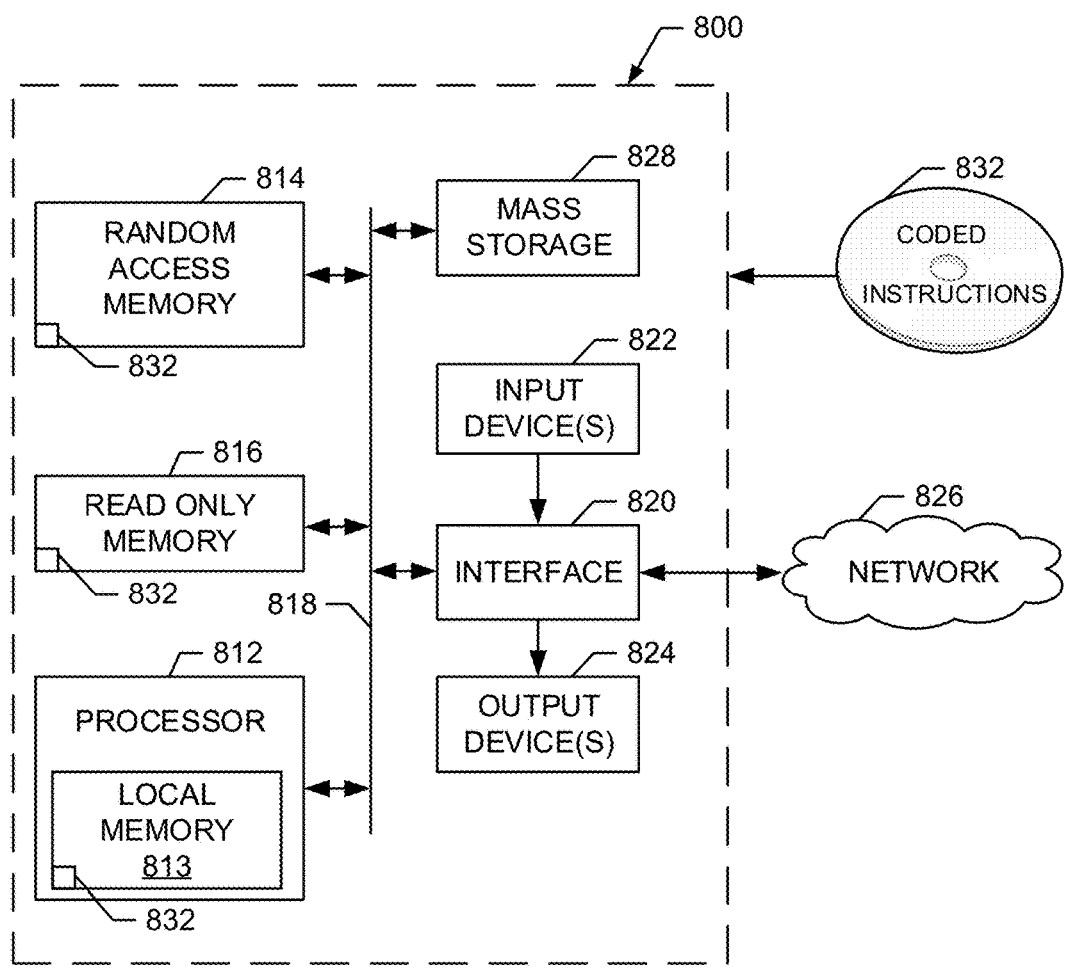
FIG. 8 shows a block diagram of an example processor system that can be used to implement systems and methods described herein.

FIG. 8 is a example diagram of an example processor platform 800 capable of executing the instructions of FIG. 7 to implement the example of FIG. 3. The processor platform 800 can be, for example, a server, a personal computer, a mobile device (e.g., a cell phone, a smart phone, a tablet such as an IPAD™), a personal digital assistant (PDA), an Internet appliance, or any other type of computing device.

The processor platform 800 of the illustrated example includes a processor 812. Processor 812 of the illustrated example is hardware. For example, processor 812 can be implemented by one or more integrated circuits, logic circuits, microprocessors or controllers from any desired family or manufacturer.

Processor 812 of the illustrated example includes a local memory 813 (e.g., a cache). Processor 812 of the illustrated example is in communication with a main memory including a volatile memory 814 and a non-volatile memory 816 via a bus 818. Volatile memory 814 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 816 can be implemented by flash memory and/or any other desired type of memory device. Access to main memory 814, 816 is controlled by a memory controller.

Processor platform 800 of the illustrated example also includes an interface circuit 820. Interface circuit 820 can be implemented by any type of interface standard, such as an Ethernet interface, a universal serial bus (USB), and/or a PCI express interface.

In the illustrated example, one or more input devices 822 are connected to the interface circuit 820. Input device(s) 822 permit(s) a user to enter data and commands into processor 812. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 824 are also connected to interface circuit 820 of the illustrated example. Output devices 824 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). Interface circuit 820 of the illustrated example, thus, typically includes a graphics driver card, a graphics driver chip or a graphics driver processor.

Interface circuit 820 of the illustrated example also includes a communication device such as a transmitter, a receiver, a transceiver, a modem and/or network interface card to facilitate exchange of data with external machines (e.g., computing devices of any kind) via a network 826 (e.g., an Ethernet connection, a digital subscriber line (DSL), a telephone line, coaxial cable, a cellular telephone system, etc.).

Processor platform 800 of the illustrated example also includes one or more mass storage devices 828 for storing software and/or data. Examples of such mass storage devices 828 include floppy disk drives, hard drive disks, compact disk drives, Blu-ray disk drives, RAID systems, and digital versatile disk (DVD) drives.

Coded instructions 832 of FIG. 7 can be stored in mass storage device 828, in volatile memory 814, in the non-volatile memory 816, and/or on a removable tangible computer readable storage medium such as a CD or DVD.

VI. Conclusion

Thus, certain examples are provided that enable calculating the water equivalent diameter of an exposed subject by defining a patient object using anterior/posterior (AP) and lateral (LAT) scout images. Pixels corresponding to air in the LAT and AP scout image are determined. Pixels outside of the air area belong to either to the patient or the table. The table for both the LAT and AP scout images is identified. The remaining pixels in the LAT AP scout images are from the patient. For each segmented object (patient or table) the boundaries of the segmented object are identified and the attenuations within the segmented boundaries are computed. The final shape and attenuation values of the patient is stored and the size-specific dose estimate (SSDE) is calculated. The water equivalent diameter value is normalized by using the technical acquisition parameters provided by the acquisition device.

This written description uses examples to disclose the subject matter, and to enable one skilled in the art to make and use the invention. The patentable scope of the subject matter is defined by the following claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A computer-implemented method to determine a water equivalent diameter of an exposed subject, the method comprising:
   receiving image data comprising one or more scout images of the exposed subject from an image acquisition device;
   identifying, using a processor, objects in the one or more scout images;
   segmenting, using a processor, the exposed subject in the one or more scout images;
   removing attenuation due to pixels corresponding to air inside the exposed subject in the one or more scout images without removing the pixels by comparing each pixel to air attenuation of a free trajectory in the one or more scout images;
   determining pixels corresponding to each object identified in the one or more scout images;
   isolating subject attenuation parameters in the one or more scout images;
   computing, using the processor, the water equivalent diameter of the exposed subject in the one or more scout images.

2. The computer-implemented method of claim 1, wherein generating the water equivalent diameter further comprises:
   storing a final shape and attenuation of the exposed subject.

3. The computer-implemented method of claim 1, wherein the water equivalent diameter is based at least in part on:
   applying a correction based on technical acquisition parameters of the image acquisition device.

4. The computer-implemented method of claim 1, wherein the method further comprises:
   receiving at least one of the scout images as a DICOM Anterior/Posterior (AP) scout image and at least one of the scout images as a DICOM Lateral (LAT) scout image.

5. The computer-implemented method of claim 1, wherein the method further comprises:
   generating a notification based on the water equivalent diameter value.

6. A computer storage device including program instructions for execution by a computing device to perform:
   receiving image data comprising one or more scout images of an exposed subject from an image acquisition device;
   identifying, using a processor, objects in the one or more scout images;
   segmenting, using a processor, the exposed subject in the one or more scout images;
   removing attenuation due to pixels corresponding to air inside the exposed subject in the one or more scout images without removing the pixels by comparing each pixel to air attenuation of a free trajectory in the one or more scout images;
   determining pixels corresponding to each object identified in the one or more scout images;
   isolating subject attenuation parameters in the one or more scout images;
   computing, using the processor, a water equivalent diameter of the exposed subject in the one or more scout images.

7. The computer storage device of claim 6, further including program instructions for execution by the computing device to perform:
   storing a final shape and attenuation of the exposed subject.

8. The computer storage device of claim 6, further including program instructions for execution by the computing device to perform:
   applying a correction based on technical acquisition parameters of the image acquisition device.

9. The computer storage device of claim 6, wherein:
   at least one of the scout images is a DICOM Anterior/Posterior (AP) scout image and at least one of the scout images is a DICOM Lateral (LAT) scout image.

10. The computer storage device of claim 6, further including program instructions for execution by the computing device to perform:
    generating a notification based on the water equivalent diameter value.

11. A system comprising a processor, the processor configured to execute computer program instructions to:
    receive image data comprising one or more scout images of an exposed subject from an image acquisition device;
    identify, using a processor, objects in the one or more scout images;
    segment, using a processor, the exposed subject in the one or more scout images;
    remove attenuation due to pixels corresponding to air inside the exposed subject in the one or more scout images without removing the pixels by comparing each pixel to air attenuation of a free trajectory in the one or more scout images;
    determine pixels corresponding to each object identified in the one or more scout images;
    isolate subject attenuation parameters in the one or more scout images;

compute, using the processor, a water equivalent diameter of the exposed subject in the one or more scout images.

12. The system of claim 11, wherein the processor is further configured to:
store a final shape and attenuation of the exposed subject.

13. The system of claim 11, wherein the processor is further configured to:
apply a correction based on technical acquisition parameters of the image acquisition device.

14. The system of claim 11, wherein:
at least one of the scout images is a DICOM Anterior/Posterior (AP) scout image and at least one of the scout images is a DICOM Lateral (LAT) scout image.

15. The system of claim 11, wherein the processor is further configured to:
generate a notification based on the water equivalent diameter value.

* * * * *